(12) United States Patent
Margalit et al.

(10) Patent No.: US 6,630,454 B2
(45) Date of Patent: Oct. 7, 2003

(54) METHOD AND PHARMACEUTICAL COMPOSITION FOR THE TREATMENT OF CANCER

(75) Inventors: Rimona Margalit, Givataim (IL); Dan Peer, Kiryat Ono (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 0 days.

(21) Appl. No.: 09/948,621

(22) Filed: Sep. 10, 2001

(65) Prior Publication Data

US 2003/0087964 A1 May 8, 2003

(51) Int. Cl.⁷ .................... A61K 31/70; A61K 31/135
(52) U.S. Cl. .................. 514/34; 514/651; 514/652
(58) Field of Search .................... 514/34, 651, 652

(56) References Cited

U.S. PATENT DOCUMENTS

| | | |
|---|---|---|
| 4,018,895 A | 4/1977 | Molloy et al. |
| 4,314,081 A | 2/1982 | Molloy et al. |
| 5,110,802 A | 5/1992 | Cantin et al. |
| 5,166,437 A | 11/1992 | Kairisalo et al. |
| 5,194,428 A | 3/1993 | Agrawal et al. |
| 5,216,141 A | 6/1993 | Benner |
| 5,776,925 A | 7/1998 | Young et al. |
| 5,859,065 A | 1/1999 | Brandes |
| 6,258,853 B1 | 7/2001 | Stowell et al. |

FOREIGN PATENT DOCUMENTS

| | | | |
|---|---|---|---|
| WO | WO 94/18961 | * 9/1994 | ............... 514/34 |
| WO | WO 99/24415 A1 | 5/1999 | |

OTHER PUBLICATIONS

Database Caplus on STN, Robert C. Byrd, Health Sciences Center, West Virginia University, Morgantown, WV, USA, Accession No. 1999–52179, Strobl et al., The Cell Death Response to .gamma.–radiation in MCF–7 cells is enhanced by a neuroleptic drug, pimozide, Abstract, Breast Cancer Research and Treatment 1998, vol. 51, No. 1, pp 83–95.
Barrows, L. R., Antineoplastic and Immunoactive Drugs, Chapter 75, pp 1236–1262;.
Cookson J, Duffett R., Fluxetine: therapeutic and undesirable effects. Hosp Med 1998 Aug.;59(8):622–626;.
Dalton, W. S., Proc. Am. Assoc. Cancer Res. 31:520–521, 1990;.
DeVita, V. T., et al., in Cancer, Principles & Practice of Oncology, 4th ed., J. B. Lippincott Co., Philadelphia, Pa., pp 2661–2664, 1993;.
Sonneveld P, Wiemer E. Inhibitors of multidrug resistance., Curr Opin Oncol 1997 Nov.;9(6):543–548;.
Tan B, Piwnica–Worms D, Ratner L., Multidrug resistance transporters and modulation. Curr. Opi n. Oncol, 2000 Sep.;12(5):450–458.
M. Abdul et al., Growth–Inhibitory Effects of Serotonin Uptake Inhibitors on Human Prostate Carcinoma Cell Lines, The Journal of Urology, vol., 154, Jul. 1995, pp. 247–250.
B.E. Bachmeier, et al., Human Keratinocyte Cell LinesDiffer in the Expression of the Collagenolytic Matrix Metalloproteinases–1,8, and —13 and of TIMP—1, Biol. Chem. vol., 381, May/Jun. 2000, pp. 509–516.
L.J. Brandes, Stimulation of Malignant Growth in Rodents by Antidepressant Drugs at Clinically Relevant Doses, Cancer Research, Jul. 1, 1992, pp. 3796–3800.
Cotterchio, et al., Antidepressant Medication Use and Breast Cancer Risk, American Journal of Epidemiology, vol. 151, No. 10, pp. 951–957.
Gupta et al., Psychotropic Drugs in Dermatology, Journal of the American Academy of Dermatology, vol. 14, No. 4, Apr. 1986, pp. 633–645.
Hemlock et al., Fluoxetine–Induced Psoriasis, The Annals of Pharmacotherapy, Feb. 1992, vol. 26, pp. 211–212.
Nordenberg et al., Effects of Psychotropic Drugs on Cell Proliferation and Differentiation, Biochemical Pharmacology, vol. 58, 199, pp. 1229–1236.
Tennyson, et al., Neurotropic and Psychotropic Drugs in Dermatology, Systemic Dermatologic Therapy, vol. 19, No. 1, Jan. 2001, pp. 179–197.
Wang et al., Antidepressant use and the risk of breast cancer: A non–association, Journal of Clinical Epidemiology, 54, (2001), 728–734.
Vindeloev, et al., A Detergent–Trypsin method for the Preparation of Nuclei for Flow Cytometric DNA Analysis, Cytometry, vol. 3, No. 5, 1983, pp. 323–327.
Xia, et al., The Antidepressants Imipramine, Clomipramine, and Citalopram Induce Apoptosis in Human Acute Myeloid Leukemia HL–60 Cells via Caspase–3 Activation, J. Biochem Molecular Toxicology, vol. 13, No. 6, 199, pp. 338–347.

* cited by examiner

Primary Examiner—Jerome D. Goldberg
(74) Attorney, Agent, or Firm—G.E. Ehrlich Ltd.

(57) ABSTRACT

A method of chemosensitization which comprises administering at least one chemotherapeutic agent and at least one 3-aryloxy-3-phenylpropylamine to a subject in need thereof.

16 Claims, 6 Drawing Sheets

METHOD AND PHARMACEUTICAL COMPOSITION FOR THE TREATMENT OF CANCER

FIELD AND BACKGROUND OF THE INVENTION

The present invention relates generally to the field of oncology, and to methods and pharmaceutical compositions for enhancing the activity of a cancer chemotherapeutic agent. More particularly, the present invention concerns the use of a 3-aryloxy-3-phenylpropylamine such as fluoxetine [(N-methyl 3-(p-trifluoromethylphenoxy)-3-phenylpropylamine] as a chemosensitizer for enhancing the cytotoxicity of a chemotherapeutic agent, especially in drug-resistant tumors and more particularly in the case of Multidrug Resistance (MDR). Methods and compositions are provided for the treatment of cancers such as, but not limited to, leukemia, lymphoma, carcinoma and sarcoma (including glioma) using a 3-aryloxy-3-phenylpropylamine, fluoxetine in particular, as a chemosensitizer.

Many of the most prevalent forms of human cancer resist effective chemotherapeutic intervention. Some tumor populations, especially adrenal, colon, jejunal, kidney and liver carcinomas, appear to have drug-resistant cells at the outset of treatment (Barrows, L. R., "Antineoplastic and Immunoactive Drugs", Chapter 75, pp 1236–1262, in: Remington: The Science and Practice of Pharmacy, Mack Publishing Co. Easton, Pa., 1995). In other cases, a resistance-conferring genetic change occurs during treatment; the resistant daughter cells then proliferate in the environment of the drug. Whatever the cause, resistance often terminates the usefulness of an antineoplastic drug.

Clinical studies suggest that a common form of multidrug resistance in human cancers results from the expression of the MDR1 gene that encodes P-glycoprotein. This glycoprotein functions as a plasma membrane, energy-dependent, multidrug efflux pump that reduces the intracellular concentration of cytotoxic drugs. This mechanism of resistance may account for de novo resistance in common tumors, such as colon cancer and renal cancer, and for acquired resistance, as observed in common hematologic tumors such as acute nonlymphocytic leukemia and malignant lymphomas. Although this type of drug resistance may be common, it is by no means the only mechanism by which cells become drug resistant. MDR is effected via an extrusion mechanism (Tan B, Piwnica-Worms D, Ratner L., Multidrug resistance transporters and modulation. Curr. Opin. Oncol, September 2000;12(5):450–8). The influx of chemotherapeutic drugs into cells is mainly by passive diffusion across the cell membrane, driven by the drug's electrochemical-potential gradient. In MDR cells there are energy-dependant extrusion channels that actively pump the drug out of the cells, reducing it's intracellular concentration below lethal threshold. The first pump identified was named Pgp (for P-glycoprotein), the second was named MRP (for Multidrug Resistant associate Protein) and several more have been identified in recent years (Tan et al. 2000, ibid.). All of them are naturally occurring proteins, and their physiological roles are assumed to involve detoxification of cells. In MDR cells they are present, for reasons yet unknown, in a significantly higher number of copies than in other non-MDR cells.

Chemical modification of cancer treatment involves the use of agents or maneuvers that are not cytotoxic in themselves, but modify the host or tumor so as to enhance anticancer therapy. Such agents are called chemosensitizers. Pilot studies using chemosensitizers indicate that these agents may reverse resistance in a subset of patients. These same preliminary studies also indicate that drug resistance is multifactorial, because not all drug-resistant patients have P-glycoprotein-positive tumor cells and only a few patients appear to benefit from the use of current chemosensitizers.

Chemosensitization research has centered on agents that reverse or modulate multidrug resistance in solid tumors (MDR1, P-glycoprotein). Chemosensitizers known to modulate P-glycoprotein function include: calcium channel blockers (verapamil, indicated for the treatment of hypertension), calmodulin inhibitors (trifluoperazine), indole alkaloids (reserpine), quinolines (quinine), lysosomotropic agents (chloroquine), steroids, (progesterone), triparanol analogs (tamoxifen), detergents (cremophor EL), and cyclic peptide antibiotics (cyclosporines, indicated to prevent host vs. graft disease) (DeVita, V. T., et al., in Cancer, Principles & Practice of Oncology, 4th ed., J. B. Lippincott Co., Philadelphia, Pa., pp 2661–2664, 1993; Sonneveld P, Wiemer E. Inhibitors of multidrug resistance., Curr Opin Oncol November 1997;9(6):543–8).

A review of studies where chemosensitizing agents were used concluded the following: (i) cardiovascular side effects associated with continuous, high-dose intravenous verapamil therapy are significant and dose-limiting; (ii) dose-limiting toxicities of the chemosensitizers, trifluoperazine and tamoxifen, was attributed to the inherent toxicity of the chemosensitizer and not due to enhanced chemotherapy toxicity; (iii) studies using high doses of cyclosporin A as a chemosensitizer found hyperbilirubinemia as a side effect; and (iv) further research is clearly needed to develop less toxic and more efficacious chemosensitizers to be used clinically (DeVita et al., 1993, ibid.).

For example, while verapamil is effective in hypertension treatment at the 2–4 $\mu$M range, for MDR reversal it requires the dose range of 10–15 $\mu$M, while at 6 $\mu$M it is already in the toxic domain.

Tumors that are considered drug-sensitive at diagnosis but acquire an MDR phenotype at relapse, pose an especially difficult clinical problem. At diagnosis, only a minority of tumor cells may express P-glycoprotein and treatment with chemotherapy provides a selection advantage for the few cells that are P-glycoprotein positive early in the course of disease. Another possibility is that natural-product-derived chemotherapy actually induces the expression of MDR1, leading to P-glycoprotein-positive tumors at relapse. Using chemosensitizers early in the course of disease may prevent the emergence of MDR by eliminating the few cells that are P-glycoprotein positive at the beginning. In vitro studies have shown that selection of drug-resistant cells by combining verapamil and doxorubicin does prevent the emergence of P-glycoprotein, but that an alternative drug resistance mechanism develops, which is secondary to altered topoisomerase II function (Dalton, W. S., Proc. Am. Assoc. Cancer Res. 31:520, 1990).

More efficacious and less toxic chemosensitizers are urgently needed to improve the outcome of chemotherapy. Clinical utility of a chemosensitizer depends upon its ability to enhance the cytotoxicity of a chemotherapeutic drug and also on its low toxicity in vivo. The present inventors have addressed these problems and provide herein a new class of chemosensitizers that permit new approaches in cancer treatment.

3-Aryloxy-3-phenylpropylamines and their use to treat depression are described in, for example, U.S. Pat. Nos.

4,018,895 and 6,258,853. Fluoxetine [(N-methyl 3-(p-trifluoromethylphenoxy)-3-phenylpropylamine], known better by its commercial name Prozac, is a well-known approved drug, indicated for psychiatric treatments (Cookson J, Duffett R., Fluoxetine: therapeutic and undesirable effects. Hosp Med August 1998;59(8):622–6). It is known to be an SSRI (Selective Serotonin Reuptake Inhibition) agent, and this activity is considered to be related to its mechanism of action in its capacity as a psychiatric drug (Cookson et al., 1998, ibid.).

3-Aryloxy-3-phenylpropylamines in general and fluoxetine in particular have not hitherto indicated as chemosensitizers for the treatment of cancer.

While reducing the present invention to practice it was unexpectedly found that fluoxetine, a member of the 3-aryloxy-3-phenylpropylamines compounds, induces a significant enhancement of the cytotoxic effect of conventional chemotherapeutic drugs at a dose range well below its toxicity limits.

SUMMARY OF THE INVENTION

The present invention provides a method of chemosensitization comprising administering at least one chemotherapeutic agent and at least one 3-aryloxy-3-phenylpropylamine to a subject in need thereof. "Chemosensitization", as used herein, means that a 3-aryloxy-3-phenylpropylamine increases or enhances the cytotoxicity of a chemotherapeutic agent compared to a level of cytotoxicity seen by that agent in the absence of 3-aryloxy-3-phenylpropylamine. That is, 3-aryloxy-3-phenylpropylamine "sensitizes" a cancer cell to the effects of the chemotherapeutic agent, allowing the agent to be more effective. 3-Aryloxy-3-phenylpropylamines are not known, and are shown herein not to have anti-cancer chemotherapeutic activity on their own.

An embodiment of the present invention is a method of treating cancer in a subject comprising administering a chemotherapeutic agent and a 3-aryloxy-3-phenylpropylamine to the subject. The cancer may be leukemia, lymphoma, carcinoma, or sarcoma. In a preferred embodiment, a patient having a form of cancer for which chemotherapy is indicated is administered a dose of 3-aryloxy-3-phenylpropylamine at intervals with each dose of the chemotherapeutic agent.

In another aspect of the invention, 3-aryloxy-3-phenylpropylamines may be used as a topical chemosensitizer. Table 1 below indicates that 5-fluorouracil, for example, is used topically for premalignant skin lesions. The inventors envision the use of 3-aryloxy-3-phenylpropylamines to enhance the cytotoxicity of topical chemotherapeutic agents.

A method for selecting a chemotherapeutic agent for which 3-aryloxy-3-phenylpropylamine is a chemosensitizer is a further embodiment of the present invention. The method comprises (i) assaying cytotoxicity of a candidate chemotherapeutic agent in the presence and in the absence of a 3-aryloxy-3-phenylpropylamine; and (ii) selecting a candidate chemotherapeutic agent as a chemotherapeutic agent for which 3-aryloxy-3-phenylpropylamine is a chemosensitizer when the cytotoxicity of the candidate agent is greater in the presence of 3-aryloxy-3-phenylpropylamine than in the absence of 3-aryloxy-3-phenylpropylamine. A presently preferred in vitro assay is the MTT cytotoxicity assay cited in the examples section. An exemplary in vivo assay is described in, for example, U.S. Pat. No. 5,776,925, which is incorporated herein by reference.

A 3-aryloxy-3-phenylpropylamine used as a chemosensitiszer in accordance with the teachings of the present invention is preferably of the formula:

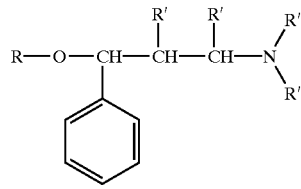

wherein each R' is independently hydrogen or methyl;
R is naphthyl or

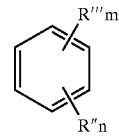

R" and R''' are halo, trifluoromethyl, $C_1$–$C_4$ alkyl, $C_1$–$C_3$ alkoxy or $C_3$–$C_4$ alkenyl; and n and m are 0, 1 or 2; and acid addition salts thereof formed with pharmaceutically acceptable acids.

In the above formula when R is naphthyl, it can be either alpha-naphthyl or beta-naphthyl. R" and R''' when they are halo, $C_1$–$C_4$ alkyl, $C_1$–$C_3$ alkyloxy or $C_3$–$C_4$ alkenyl represent, illustratively, the following atoms or groups: fluoro, chloro, bromo, iodo, methyl, ethyl, isopropyl, n-propyl, n-butyl, isobutyl, sec-butyl, t-butyl, methoxy, ethoxy, n-propoxy, isopropoxy, allyl, methallyl, crotyl and the like. R thus can represent o, m and p-trifluoromethylphenyl, o, m and p-chlorophenyl, o, m and p-bromophenyl, o, m and p-fluorophenyl, o, m and p-tolyl, xylyl including all position isomers, o, m and p-anisyl, o, m and p-allylphenyl, o, m and p-methylallylphenyl, o, m and p-phenetolyl(ethoxyphenyl), 2,4-dichlorophenyl, 3,5-difluorophenyl, 2-methoxy-4-chlorophenyl, 2-methyl-4-chlorophenyl, 2-ethyl-4-bromophenyl, 2,4,6-trimethylphenyl, 2-fluoro-4-trifluoromethylphenyl, 2,4,6-trichlorophenyl, 2,4,5-trichlorophenyl and the like.

Also included within the scope of this invention are the pharmaceutically-acceptable salts of the amine bases represented by the above formula formed with non-toxic acids. These acid addition salts include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylates, phenyl-substituted alkanoates, hydroxy alkanoates and alkanedioates, aromatic acids, aliphatic and aromatic sulfonic acids etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluorodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, beta-hydroxybutyrate, glycollate, malate, tartrate, methanesulfonate, propanesulfonates, naphthalene-1-sulfonate, naphthalene-2-sulfonate, mandelate and the like salts.

Compounds illustrative of the scope of this invention include the following:

3-(p-isopropoxyphenxoy)-3-phenylpropylamine methanesulfonate;
N,N-dimethyl 3-(3',4'-dimethoxyphenoxy)-3-phenylpropylamine p-hydroxybenzoate;
N,N-dimethyl 3-(alpha-naphthoxy)-3-phenylpropylamine bromide;
N,N-dimethyl 3-(beta-naphthoxy)-3-phenyl-1-methylpropylamine iodide;
3-(2'-methyl-4',5'-dichlorophenoxy)-3-phenylpropylamine nitrate;
3-(p-t-butylphenoxy)-3-phenylpropylamine glutarate;
N-methyl 3-(2'-chloro-p-tolyloxy)-3-phenyl-1-methylpropylamine lactate;
3-(2',4'-dichlorophenoxy)-3-phenyl-2-methylpropylamine citrate;
N,N-dimethyl 3-(m-anisyloxy)-3-phenyl-1-methylpropylamine maleate;
N-methyl 3-(p-tolyloxy)-3-phenylpropylamine sulfate;
N,N-dimethyl 3-(2',4'-difluorophenoxy)-3-phenylpropylamine 2,4-dinitrobenzoate;
3-(o-ethylphenoxy)-3-phenylpropylamine dihydrogen phosphate;
N-methyl-(2'-chloro-4'-isopropylphenoxy)-3-phenyl-2-methylpropylamine maleate;
N,N-dimethyl 3-(2'-alkyl-4'-fluorophenoxy)-3-phenylpropylamine succinate;
N,N-dimethyl 3-(o-isopropoxyphenoxy)-3-phenyl-propylamine phenylacetate;
N,N-dimethyl 3-(o-)bromophenoxy)-3-phenyl-propylamine beta-phenylpropionate;
N-methyl 3-(p-iodophenoxy)-3-phenyl-propylamine propiolate;
N-methyl 3-(3-n-propylphenoxy)-3-phenyl-propylamine decanoate; and preferably,
N-methyl 3-(p-trifluoromethylphenoxy)-3-phenylpropylamine.

The present invention successfully addresses the shortcomings of the presently known configurations by identifying a new chemosensitizer which efficiently act at concentrations well below its toxicity and which is of particular efficacy in chemosensitizing multi drug resistant (MDR) cells.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
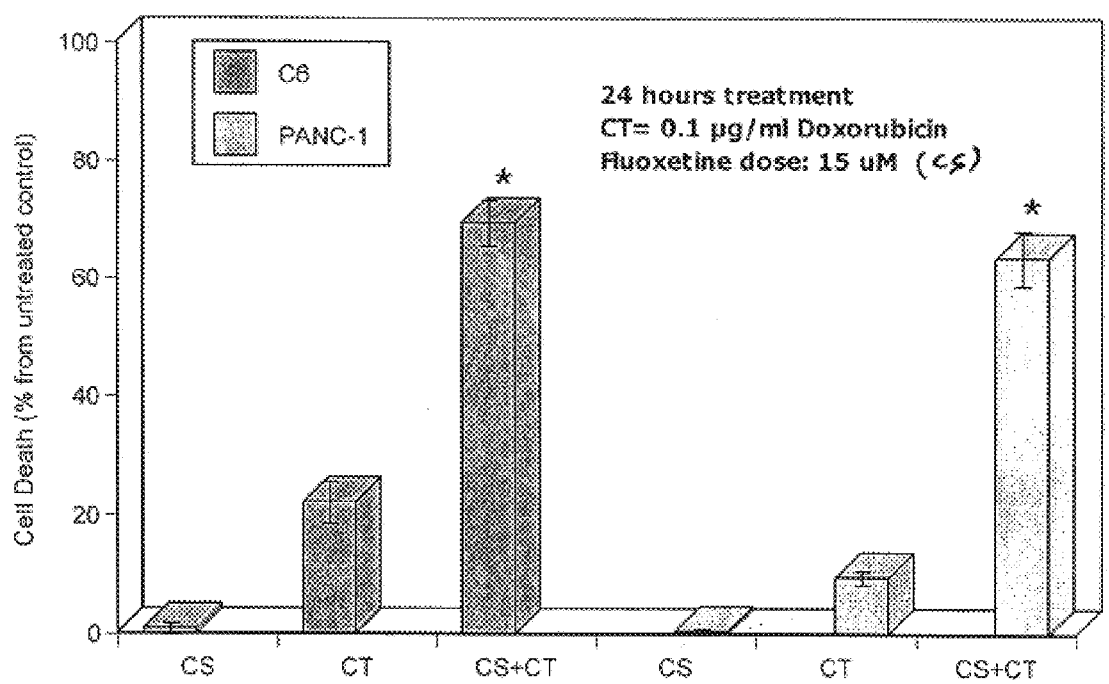
FIG. 1 is a bar graph demonstrating the increase in death of C6 cells and, separately, PANC-1 cells (% from untreated control) as a function of treatment media, at 24 hours post administration. CS—15 $\mu$M fluoxetine alone, CT—0.1 $\mu$g/ml doxorubicin alone, CT+CS—combination of the two. Each bar is an average of 32–64 repeats, and the error bars represent the standard deviations. The star (*) indicates statistical significance P<0.001 (two-tails student t-test) compared to the treatment with the chemotherapeutic drug alone.

The present invention is of methods and pharmaceutical compositions which can be used in chemosensitization. Specifically, the present invention can be used to render cancer cells more sensitive to chemotherapeutic agents, hence increase the cytotoxic effect of such agents on cells.

The principles and operation of a method and pharmaceutical composition according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present invention results from the discovery that 3-aryloxy-3-phenylpropylamines act as efficient chemosensitizers at non-toxic concentrations. Chemosensitization using a 3-aryloxy-3-phenylpropylamine refers to an enhancement of cytotoxicity on the part of a chemotherapeutic agent when that agent is administered in conjunction with administering a 3-aryloxy-3-phenylpropylamine.

Hence, the invention relates to a novel treatment for effecting tumor (both solid and non-solid) chemotherapy, based on the combination of at least one chemotherapeutic drug that are standard therapy protocols in the clinic such as, but not limited to, Doxorubicin, Vinblastine and Mitomycin C; and at least one 3-aryloxy-3-phenylpropylamine, preferably fluoxetine (Prozac), a drug approved and widely used for psychiatric situations such as depression. It is shown herein that a combined treatment of at least one chemotherapeutic drug and at least one 3-aryloxy-3-phenylpropylamine leads to significant increases in efficacy of the cytotoxic drugs, up to 5-fold for a single dose, and at doses well below safety limits. Moreover, the novel treatment is especially effective in tumors that are resistant (MDR) to the chemotherapeutic drugs. Other reversal agents cannot be used in the clinic due to their toxicity at the required dose levels. In addition, 3-aryloxy-3-phenylpropylamines, such as fluoxetine, can be administered orally, which is easier on the patient, and its "side effect" of mood improvement will also be beneficial to the cancer patient.

According to the present invention the chemotherapeutic agent may be, for example, one of the following: an alkylating agent such as a nitrogen mustard, an ethylenimine and a methylmelamine, an alkyl sulfonate, a nitrosourea, and a triazene; an antimetabolite such as a folic acid analog, a pyrimidine analog, and a purine analog; a natural product such as a vinca alkaloid, an epipodophyllotoxin, an antibiotic, an enzyme, a taxane, and a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Specific examples of alkylating agents, antimetabolites, natural products, miscellaneous agents, hormones and antagonists, and the types of cancer for which these classes of chemotherapeutic agents are indicated are provided in Table 1. Preferably, the chemotherapeutic agent is a nitrogen mustard, an epipodophyllotoxin, an antibiotic, or a platinum coordination complex. A more preferred chemotherapeutic agent is bleomycin, doxorubicin, paclitaxel, etoposide, 4-OH cyclophosphamide, or cisplatinum. A presently preferred chemotherapeutic agent is doxorubicin, mitmycin C or bleomycin.

3-aryloxy-3-phenylpropylamine compounds, methods for making and methods for using them are described in U.S. Pat. Nos. 4,018,895, 4,314,081, 5,166,437 and 6,258,853 which are incorporated by reference herein, and further below.

3-Aryloxy-3-phenylpropylamines used as chemosensitizers may be administered before together with or after administration of the chemotherapeutic agent. Administration of the 3-aryloxy-3-phenylpropylamine after the chemotherapeutic agent is presently preferred. The 3-aryloxy-3-phenylpropylamine may be administered as a single dose, or it may be administered as two or more doses separated by an interval of time. The 3-aryloxy-3-phenylpropylamine may be administered from about one minute to about 12 hours following administration of the chemotherapy agent, preferably from about 5 minutes to about 5 hours. Where the 3-aryloxy-3-phenylpropylamine is administered as two or more doses, the time interval between the 3-aryloxy-3-phenylpropylamine administrations may be from about one minute to about 12 hours, preferably from about 5 minutes to about 5 hours, more preferably about 4 to 5 hours. The dosing protocol may be repeated; from one to three times, for example. Administration may be intravenous, intraperitoneal, parenteral, intramuscular, subcutaneous, oral, or topical, with topical and intravenous administration being preferred, and intravenous being more preferred.

The 3-aryloxy-3-phenylpropylamine to be used in the method of the invention will be administered in a pharmaceutically/therapeutically effective amount. By "pharmaceutically/therapeutically effective" is meant that dose which will provide an enhanced toxicity to a chemotherapeutic agent. The specific dose will vary depending on the particular 3-aryloxy-3-phenylpropylamine chosen, the dosing regimen to be followed, and the particular chemotherapeutic agent with which it is administered. Such dose can be determined without undue experimentation by methods known in the art or as described herein.

One of skill in the art in light of the present disclosure would realize flexibility in the above regimen and would be able to test, without undue experimentation, for optimal timing and dosage for administration of a 3-aryloxy-3-phenylpropylamine for a particular circumstance.

A 3-aryloxy-3-phenylpropylamine for use as a chemosensitizer may have structure I:

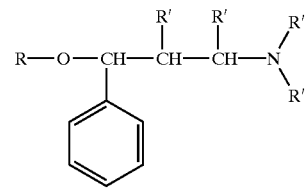

wherein each R' is independently hydrogen or methyl;
R is naphthyl or

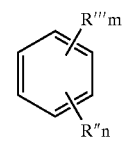

R" and R''' are halo, trifluoromethyl, $C_1$–$C_4$ alkyl, $C_1$–$C_3$ alkoxy or $C_3$–$C_4$ alkenyl; and n and m are 0, 1 or 2; and acid addition salts thereof formed with pharmaceutically acceptable acids.

In the above formula when R is naphthyl, it can be either alpha-naphthyl or beta-naphthyl. R" and R''' when they are halo, $C_1$–$C_4$ alkyl, $C_1$–$C_3$ alkyloxy or $C_3$–$C_4$ alkenyl represent, illustratively, the following atoms or groups: fluoro, chloro, bromo, iodo, methyl, ethyl, isopropyl, n-propyl, n-butyl, isobutyl, sec-butyl, t-butyl, methoxy, ethoxy, n-propoxy, isopropoxy, allyl, methallyl, crotyl and the like. R thus can represent o, m and p-trifluoromethylphenyl, o, m and p-chlorophenyl, o, m and p-bromophenyl, o, m and p-fluorophenyl, o, m and p-tolyl, xylyl including all position isomers, o, m and p-anisyl, o, m and p-allylphenyl, o, m and p-methylallylphenyl, o, m and p-phenetolyl(ethoxyphenyl), 2,4-dichlorophenyl, 3,5-difluorophenyl, 2-methoxy-4chlorophenyl, 2-methyl-4-chlorophenyl, 2-ethyl-4-bromophenyl, 2,4,6-trimethylphenyl, 2-fluoro-4-trifluoromethylphenyl, 2,4,6-trichlorophenyl, 2,4,5-trichlorophenyl and the like.

Also included within the scope of this invention are the pharmaceutically-acceptable salts of the amine bases represented by the above formula formed with non-toxic acids. These acid addition salts include salts derived from inorganic acids such as: hydrochloric acid, nitric acid, phosphoric acid, sulfuric acid, hydrobromic acid, hydriodic acid, nitrous acid, phosphorous acid and the like, as well as salts of non-toxic organic acids including aliphatic mono and dicarboxylates, phenyl-substituted alkanoates, hydroxy alkanoates and alkanedioates, aromatic acids, aliphatic and aromatic sulfonic acids etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluorodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, beta-hydroxybutyrate, glycollate, malate, tartrate, methanesulfonate, propanesulfonates, naphthalene-1-sulfonate, naphthalene-2-sulfonate, mandelate and the like salts.

Compounds illustrative of the scope of this invention include the following:

3-(p-isopropoxyphenxoy)-3-phenylpropylamine methane-sulfonate;
N,N-dimethyl 3-(3',4'-dimethoxyphenoxy)-3-phenylpropylamine p-hydroxybenzoate;
N,N-dimethyl 3-(alpha-naphthoxy)-3-phenylpropylamine bromide;
N,N-dimethyl 3-(beta-naphthoxy)-3-phenyl-1-methylpropylamine iodide;
3-(2'-methyl-4',5'-dichlorophenoxy)-3-phenylpropylamine nitrate;
3-(p-t-butylphenoxy)-3-phenylpropylamine glutarate;
N-methyl 3-(2'-chloro-p-tolyloxy)-3-phenyl-1-methylpropylamine lactate;
3-(2',4'-dichlorophenoxy)-3-phenyl-2-methylpropylamine citrate;
N,N-dimethyl 3-(m-anisyloxy)-3-phenyl-1-methylpropylamine maleate;
N-methyl 3-(p-tolyloxy)-3-phenylpropylamine sulfate;
N,N-dimethyl 3-(2',4'-difluorophenoxy)-3-phenylpropylamine 2,4-dinitrobenzoate;
3-(o-ethylphenoxy)-3-phenylpropylamine dihydrogen phosphate;
N-methyl-(2'-chloro-4'-isopropylphenoxy)-3-phenyl-2-methylpropylamine maleate;
N,N-dimethyl 3-(2'-alkyl-4'-fluorophenoxy)-3-phenylpropylamine succinate;
N,N-dimethyl 3-(o-isopropoxyphenoxy)-3-phenyl-propylaminephenylacetate;
N,N-dimethyl 3-(o-)bromophenoxy)-3-phenyl-propylamine beta-phenylpropionate;
N-methyl 3-(p-iodophenoxy)-3-phenyl-propylamine propiolate;
N-methyl 3-(3-n-propylphenoxy)-3-phenyl-propylamine decanoate; and preferably,
N-methyl 3-(p-trifluoromethylphenoxy)-3-phenylpropylamine.

The 3-aryloxy-3-phenylpropylamines of this invention in the form of their free bases are high boiling oils, but white crystalline solids in the form of their acid addition salts. The compounds can be prepared in several ways. A particularly useful procedure for preparing compounds represented by the above formula (in which both R' groups attached to the nitrogen are methyl) involves the reduction of beta-dimethylaminopropiophenone produced by a Mannich reaction to yield N,N-dimethyl 3-phenyl-3-hydroxypropylamine. Replacement of the hydroxyl group with a halogen, such as chlorine, yields the corresponding N,N-dimethyl 3-phenyl-3-chloropropylamine. Reaction of this chloro compound with a suitably substituted phenol, as for example o-methoxyphenol (guiacol), produces a compound of this invention in which both R' groups are methyl. Treatment of the N,N-dimethyl compound with cyanogen-bromide serves to replace one N-methyl group with a cyano group. Hydrolysis of the resulting compound with base yields a compound of this invention in which only one R' group on the nitrogen is methyl. For example, treatment of N,N-dimethyl 3-(o-anisyloxy)-3-phenylpropylamine with cyanogen bromide followed by alkaline hydrolysis of the N-cyano compound yields directly N-methyl 3-(o-anisyloxy)-3-phenylpropylamine [N-methyl 3-(o-methoxy phenoxy)-3-phenylpropylamine].

An alternate preparation of the compounds of this invention in which only one of the R' groups attached to the nitrogen is methyl is carried as follows:

3-Chloropropylbenzene is reacted with a positive halogenating agent such N-bromosuccinimide to yield the corresponding 3-chloro-1-bromopropylbenzene. Selective replacement of the bromo atom with the sodium salt of a phenol, as for example, the sodium salt of o-methoxyphenol (guiacol) yields a 3-chloro-1-(1-methoxyphenoxy)-propylbenzene [also named as 3-chloro-1-(o-anisyloxy) propylbenzene]. Reaction of the 3-chloro derivative thus produced with methylamine yields the desired N-methyl 3-(o-anisyloxy)-3-phenylpropylamine.

3-Aryloxy-3-phenylpropylamine compounds in which both R' groups attached to the nitrogen in the above formula are hydrogen can be prepared from an intermediate produced in the previous preparation of the N-methyl compounds such as, for illustrative purposes, 3-chloro-1-(o-anisyloxy)-propylbenzene prepared by the reaction of 3-chloro-1-bromobenzene and sodium guiacol. This chloro compound is reacted with sodium azide to give the corresponding 3-azido-1-(o-anisyloxy)-propylbenzene. Reduction of the azide group with a metallo-organic reducing agent such as sodium borohydride yields the desired primary amine. Alternatively, the chloro compound can be reacted directly with a large excess of ammonia in a high pressure reactor to give the primary amine.

3-Aryloxy-3-phenylpropylamine compounds in which the R' group on the carbon atom alpha to the nitrogen is methyl can be prepared by reacting phenyl 2'-propenyl ketone with dimethylamine [See J. Am. Chem. Soc., 75, 4460 (1953)]. The resulting 3-dimethylaminobutyrophenone is reduced to yield the N,N-dimethyl 3-hydroxy-1-methyl-3-phenylpropylamine. Replacement of the hydroxyl with chlorine followed by reaction of the chloro-compound with the sodium salt of a suitably substituted phenol yields the N,N-dimethyl derivatives of this invention bearing an alpha methyl group on the propylamine backbone of the molecule. Production of the corresponding N-methyl derivative can be accomplished by the aforementioned reaction sequence utilizing cyanogen bromide. The N-methyl derivative can in turn be converted to the corresponding primary amine (in which both R' groups on the nitrogen are hydrogen) by oxidation in neutral permanganate according to the procedure of Booher and Pohland, Ser. No. 317,969, filed Dec. 26, 1972. Compounds in which the R' group attached to the beta-carbon atom is methyl are prepared by a Mannich reaction involving propiophenone, formaldehyde and dimethylamine. The resulting ketone, an alpha-methyl-beta-dimethylaminopropiophenone, is subjected to the same reduction procedure as before to yield a hydroxy compound. Replacement of the hydroxyl with chlorine followed by reaction of the chloro compound with the sodium salt of a phenol yields a dimethyl amine compound of this invention. Conversion of the dimethylamine to the corresponding monomethyl and primary amines is carried out as before.

Those 3-aryloxy-3-phenylpropylamine compounds in which the R' group attached to either the alpha or beta-carbon is methyl have two asymmetric carbon atoms, the carbon carrying the R' methyl and the .gamma.-carbon carrying the phenoxy and phenyl groups. Thus, such compounds exist in four diastereomeric forms occurring as two racemic pairs, the less soluble pair being designated alpha-dl form and the more soluble the beta-dl form. Each racemate can be resolved into its individual d and l isomers by methods well known in the art, particularly, by forming salts with optically active acids and separating the salts by crystallization.

A 3-aryloxy-3-phenylpropylamine may be coupled to a site-directing molecule to form a conjugate for targeted in vivo delivery. "Site-directing" means having specificity for targeted sites. "Specificity for targeted sites" means that upon contacting the 3-aryloxy-3-phenylpropylamine-site-directing-conjugate with the targeted site, for example, under physiological conditions of ionic strength, temperature, pH and the like, specific binding will occur. The interaction may occur due to specific electrostatic, hydrophobic, entropic or other interaction of certain residues of the conjugate with specific residues of the target to form a stable complex under conditions effective to promote the interaction. Exemplary site-directing molecules contemplated in the present invention include but are not limited to: oligonucleotides, polyamides including peptides having affinity for a biological receptor and proteins such as antibodies; steroids and steroid derivatives; hormones such as estradiol, or histamine; hormone mimics such as morphine; and further macrocycles such as sapphyrins and rubyrins.

As used herein, a "site-directing molecule" may be an oligonucleotide, an antibody, a hormone, a peptide having affinity for a biological receptor, a sapphyrin molecule, and the like. A preferred site-directing molecule is a hormone, such as estradiol, estrogen, progesterone, and the like. A site-directing molecule may have binding specificity for localization to a treatment site and a biological receptor may be localized to a treatment site. A 3-aryloxy-3-phenylpropylamine oligonucleotide-conjugate, where the oligonucleotide is complementary to an oncogenic messenger RNA, for example, would further localize chemotherapeutic activity to a particularly desired site. Antisense technology is discussed in U.S. Pat. Nos. 5,194,428, 5,110,802 and 5,216,141, all of which are incorporated by reference herein.

A couple may be described as a linker, i.e., the covalent product formed by reaction of a reactive group designed to attach covalently another molecule at a distance from the 3-aryloxy-3-phenylpropylamine macrocycle. Exemplary linkers or couples are amides, amine, thiol, thioether, ether, or phosphate covalent bonds. In most preferred embodiments, site-directing molecules are covalently bonded to the 3-aryloxy-3-phenylpropylamine via a carbon-nitrogen, carbon-sulfur, or a carbon-oxygen bond.

Generally, water soluble 3-aryloxy-3-phenylpropylamines retaining lipophilicity are preferred for the applications described herein. "Water soluble" means soluble in aqueous fluids to about 1 mM or better. "Retaining lipophilicity" means having greater affinity for lipid rich tissues or materials than surrounding nonlipid rich tissues. "Lipid rich" means having a greater amount of triglyceride, cholesterol, fatty acids or the like.

Representative examples of useful steroids include any of the steroid hormones of the following five categories: progestins (e.g. progesterone), glucocorticoids (e.g., cortisol), mineralocorticoids (e.g., aldosterone), androgens (e.g., testosterone) and estrogens (e.g., estradiol).

Representative examples of useful amino acids of peptides or polypeptides include amino acids with simple aliphatic side chains (e.g., glycine, alanine, valine, leucine, and isoleucine), amino acids with aromatic side chains (e.g., phenylalanine, tryptophan, tyrosine, and histidine), amino acids with oxygen and sulfur-containing side chains (e.g., serine, threonine, methionine, and cysteine), amino acids with side chains containing carboxylic acid or amide groups (e.g., aspartic acid, glutamic acid, asparagine, and glutamine), and amino acids with side chains containing strongly basic groups (e.g., lysine and arginine), and proline. Representative examples of useful peptides include any of both naturally occurring and synthetic di-, tri-, tetra-, pentapeptides or longer peptides derived from any of the above described amino acids (e.g., endorphin, enkephalin, epidermal growth factor, poly-L-lysine, or a hormone). Representative examples of useful polypeptides include both naturally occurring and synthetic polypeptides (e.g., insulin, ribonuclease, and endorphins) derived from the above described amino acids and peptides.

The term "a peptide having affinity for a biological receptor" means that upon contacting the peptide with the biological receptor, for example, under appropriate conditions of ionic strength, temperature, pH and the like, specific binding will occur. The interaction may occur due to specific electrostatic, hydrophobic, entropic or other interaction of certain amino acid or glycolytic residues of the peptide with specific amino acid or glycolytic residues of the receptor to form a stable complex under the conditions effective to promote the interaction. The interaction may alter the three-dimensional conformation and the function or activity of either or both the peptide and the receptor involved in the interaction. A peptide having affinity for a biological receptor may include an endorphin, an enkephalin, a growth factor, e.g. epidermal growth factor, poly-L-lysine, a hormone, a peptide region of a protein and the like. A hormone may be estradiol, for example.

For use as a chemosensitizer, 3-aryloxy-3-phenylpropylamines are provided as pharmaceutical preparations. A pharmaceutical preparation of a 3-aryloxy-3-phenylpropylamine may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a 3-aryloxy-3-phenylpropylamine of the present invention and the pharmaceutically acceptable carriers are then easily administered in a variety of dosage forms such as injectable solutions.

For parenteral administration, solutions of the 3-aryloxy-3-phenylpropylamine in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy use with a syringe exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars such as mannitol or dextrose or sodium chloride. A more preferable isotonic agent is a mannitol solution of about 2–8% concentration, and, most preferably, of about 5% concentration. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

3-Aryloxy-3-phenylpropylamines may be co-formulated with a chemotherapeutic agent. Methods of co-formulating more than a single active ingredient are well known in the art. Such co-formulation ensures co-administration of the chemotherapeutic agent and the 3-aryloxy-3-phenylpropylamine.

The present inventors envision that 3-aryloxy-3-phenylpropylamines may be used as chemosensitizers for enhancing the cytotoxicity of a variety of chemotherapeutic agents having differing mechanisms of action. A listing of currently available chemotherapeutic agents according to class, and including diseases for which the agents are indicated, is provided as Table 1.

TABLE 1

Chemotherapeutic Agents Useful in Neoplastic Disease[1]

| Class | Type of Agent | Name | Disease[2] |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | lphalan | Multiple myeloma, breast, ovary |
| | | dorambucil | Chronic lymphocytic leukemia, primary macroglobulinemia, Hodgkin's disease, non-Hodgkin's lymphomas |
| | | Estramustine | Prostate |
| | Ethylenimines and Methylmelamines | Hexamethyl-melamine | Ovary |
| | | Thiotepa | Bladder, breast, ovary |
| | Alkyl Sulfonates | Busulfan | Chronic granulocytic leukemia |
| | Nitrosoureas | Carmustine | Hodgkin's disease, non-Hodgkin's lymphomas, primary brain tumors, multiple myeloma, malignant melanoma |

TABLE 1-continued

Chemotherapeutic Agents Useful in Neoplastic Disease[1]

| Class | Type of Agent | Name | Disease[2] |
|---|---|---|---|
| | | Lomustine | Hodgkin's disease, non-Hodgkin's lymphomas, primary brain tumors, small-cell lung |
| | | Semustine | Primary brain tumors, stomach, colon |
| | | Streptozocin | Malignant pancreatic insulinoma, malignant carcinoid |
| | Triazenes | Dacarbazine | Malignant melanoma, Hodgkin's disease, soft-tissue sarcomas |
| | | Procarbazine | |
| | | Aziridine | |
| Antimetabolites | Folic Acid Analogs | Methotrexate Trimetrexate | lymphocytic leukemia, choriocarcinoma, mycosis fungoides, breast, head and neck, lung, osteogenic sarcoma |
| | Pyrimidine Analogs | Fluorouracil | Breast, colon, stomach, pancreas, |
| | | Floxuridine | ovary, bead and neck, urinary bladder, premalignant skin lesions (topical) |
| | Purine Analogs and Related Inhibitors | Cytarabine Azacitidine Mercaptopurine | Acute granulocytic and acute lymphocytic leukemias lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non-Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | | Vindesine | Vinca-resistant acute lymphocytic leukemia, chronic myelocytic leukemia, melanoma, lymphomas, breast |
| | Epipodophyl-Lotoxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |
| | | Doxorubicin 4'-Deoxydoxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas |
| | | Plicamycin | Testis, malignant hypercalcemia |
| | | Mitomycin | Stomach, cervix, colon, breast, pancreas, bladder, head and neck |
| | Enzymes | Asparaginase | Acute lymphocytic leukemia |
| | Taxanes | Docetaxel Paclitaxel | Breast, ovarian |
| | Biological Response Modifiers | Interferon Alfa | Hairy cell leukemia, Kaposi's sarcoma, melanoma, carcinoid, cell, ovary, bladder, |

TABLE 1-continued

Chemotherapeutic Agents Useful in Neoplastic Disease[1]

| Class | Type of Agent | Name | Disease[2] |
|---|---|---|---|
| | | | non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin Carboplatin | Testis, ovary, bladder, head and neck, lung, thyroid, cervix, endometrium, neuroblastoma, osteogenic sarcoma |
| | Anthracanedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine | Hodgkin's disease |
| | Adrenocortical Suppressant | Mitotane Aminoglutethimide | Adrenal cortex Breast |
| Hormones and Antagonists | costeroids | | Acute and chronic lymphocytic leukemias, non-Hodgkin's lymphomas, Hodgkin's disease, breast |
| | Progestins | Hydroxy-progesterone caproate Medroxy-progesterone acetate Megestrol acetate | Endometrium, breast |
| | Estrogens | Diethylstilbestrol Ethinyl estradiol | Breast, prostate |
| | Antiestrogen Androgens | Tamoxifen tosterone propionate Fluoxymesterone | |
| | Antiandrogen | Flutamide | Prostate |
| | Gonadotropin-Releasing hormone analog | Leuprolide Goserelin | Prostate, Estrogen-receptor-positive breast |

[1]Adapted from Calabresi, P., and B. A. Chabner, "Chemotherapy of Neoplastic Diseases" Section XII, pp 1202–1263 in: Goodman and Gilman's The Pharmacological Basis of Therapeutics, Eighth ed., 1990 Pergamin Press, Inc.; and Barrows, L. R., "Antineoplastic and Immunoactive Drugs", Chapter 75, pp 1236–1262, in: Remington: The Science and Practice of Pharmacy, Mack Publishing Co. Easton, PA, 1995.; both references are incorporated by reference herein, in particular for treatment protocols.
[2]Neoplasms are carcinomas unless otherwise indicated.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Hence, additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Methods

Chemotherapies (CT):
  Mitomycin C (MMC), Vinblastine (VIN) and Doxorubicin (DOX). Chemosensitizer (CS): fluoxetine.

Cell Lines:

MCF-7 (human breast carcinoma), HT1080 (human fibrosarcoma), U2OS (human osteosarcoma) PANC-1 (human pancreatic adenocarcinoma) and C6 (rat glioblastoma).

Cell Culture Growth and Maintenance Media:

Dulbecco's modified Eagle's medium (DMEM) supplemented with 10% fetal calf serum (FCS), Penicillin (10,000 units/ml), Streptomycin (10 mg/ml) and L-Glutamine (200 mM)

Cell Cultures:

Cells were grown in monolayers in 100×20 mm dishes, in the growth media listed above, at 37° C. in 5% $CO_2$.

Cell Survival:

Cells were grown in monolayers as describe above and seeded onto 96 multiwell plates at a density of $1\times10^4$ cells/ml, 24 hours prior to an experiment. Twenty four hours later, the media was replaced by treatment media as is detailed in the Experimental Results section that follows. The experiments were terminated 24 or 48 hours post media replacement. The quantity of viable cells was determined by the MTT test, recording the absorbencies in a plate reader, at two wavelength: 550 and 650 nm.

Drug Efflux:

Cells were grown in monolayers as described above. Several days prior to an experiment the cells (at a density in the range of $5\times10^4$–$5\times10^5$ cells/ml) were seeded into 24 multiwell culture plates. The experiments were performed when the cells reached semi-confluency. The efflux experiments were conducted according to the following protocol: Cells were loaded, by incubation for 10 hours, with either a non-lethal dose of DOX, or the same DOX dose combined with fluoxetine. Control cells received media alone. At the end of the incubation, the media was removed, the cells washed with buffer, and thereafter incubated with either media alone (for the wells incubated with DOX only) or media with fluoxetine at the same dose as in the 10 hours incubation. At selected time points, the medium from every well was collected and replaced with a fresh similar medium. At the end of the experiment the cells in each well were dissolved by adding 5% Deoxycholate (DOC) to each well. Samples from the media collected at each time point, and samples from the final detergent-dissolved cells, were transferred to a 96 well plate suitable for a fluorimeter plate reader. Excitation and emission were at 480 nm and 530 nm, respectively. Calibration curves were run with each assay using DOX standards dissolved in the appropriate media (i.e., buffer or buffer/DOC).

Experimental Results

Testing the Response of MDR Cell Lines to a Single Fluoxetine Dose

C6 and, in separate experiments, PANC-1 cells were seeded onto multiwell (96) culture plates, and the experiments were initiated when the cells reached semi-confluency. The serum-supplemented cell growth media was replaced by a treatment media, selected from: (i) the combination of a chemotherapeutic drug and fluoxetine dissolved in serum supplemented growth media; (ii) chemotherapeutic drug dissolved in serum supplemented growth media (iii) fluoxetine dissolved in serum supplemented growth media; and (iv) serum supplemented growth media alone (untreated control). Drug species and dose were the same in (i) and (ii). Fluoxetine dose was the same in (i) and (iii). The experiment was terminated 24 hours later, and the number of viable cells was quantitated using the MTT method.

Figure 2:
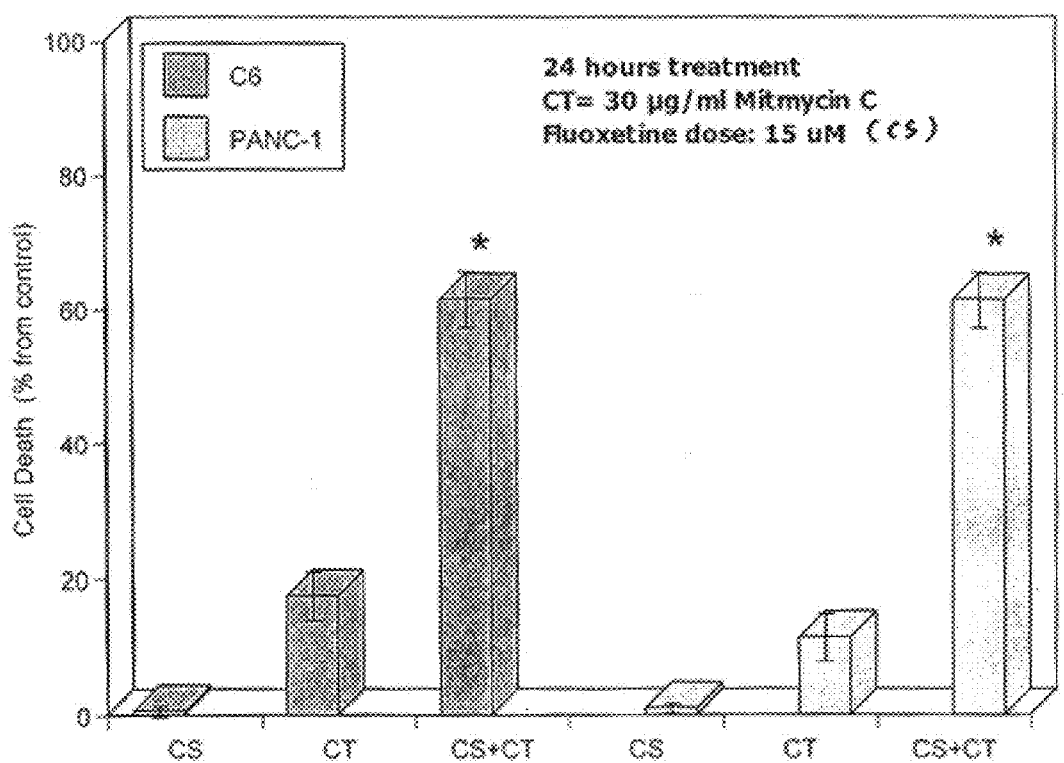
FIG. 2 is a bar graph demonstrating the increase in death of C6 cells and, separately, PANC-1 cells (% from untreated control) as a function of treatment media, at 24 hours post administration. CS—15 $\mu$M fluoxetine alone, CT—30 $\mu$g/ml mitomycin C alone, CT+CS—combination of the two. Each bar is an average of 32–64 repeats, and the error bars represent the standard deviations. The star (*) indicates statistical significance P<0.01 (two-tails student t-test) compared to the treatment with the chemotherapeutic drug alone.

Typical results, showing the effects of the various treatment groups on cell death are shown in FIGS. 1 and 2, for both cell lines and for the chemotherapeutic drugs mitmycin C (MMC) and doxorubicin (DOX), respectively. The fluoxetine dose used in these experiments matches the highest safe dose used for accepted indications of fluoxetine. The data clearly shows that fluoxetine alone does not affect cell survival at all. At the drug doses applied (listed in FIGS. 1 and 2), treatment with drug alone was only mildly effective in causing cell death, at its best no more than 20%. In contrast, for the four cases studied (2 drugs, 2 cell lines), the combination treatment caused a significant enhancement in cell death, which was 3–4 fold, clearly showing the effectiveness of the combination treatment.

Evaluating Fluoxetine Dose Response

Studies similar in general to those outlined in the previous section, were conducted with five cell lines selected for this task (PANC-1, C6, MCF-7, U2OS and HT1080), increasing the length of the experiment to 48 hours. The studies were done with DOX and with Vinblastine (VIN or VLB). The treatment groups were similar to those listed in the previous sections, with the following additions: a series of fluoxetine doses were tested, alone and in combination with the cytotoxic drugs, covering a fluoxetine range of 0–15 $\mu$M.

Figure 3:
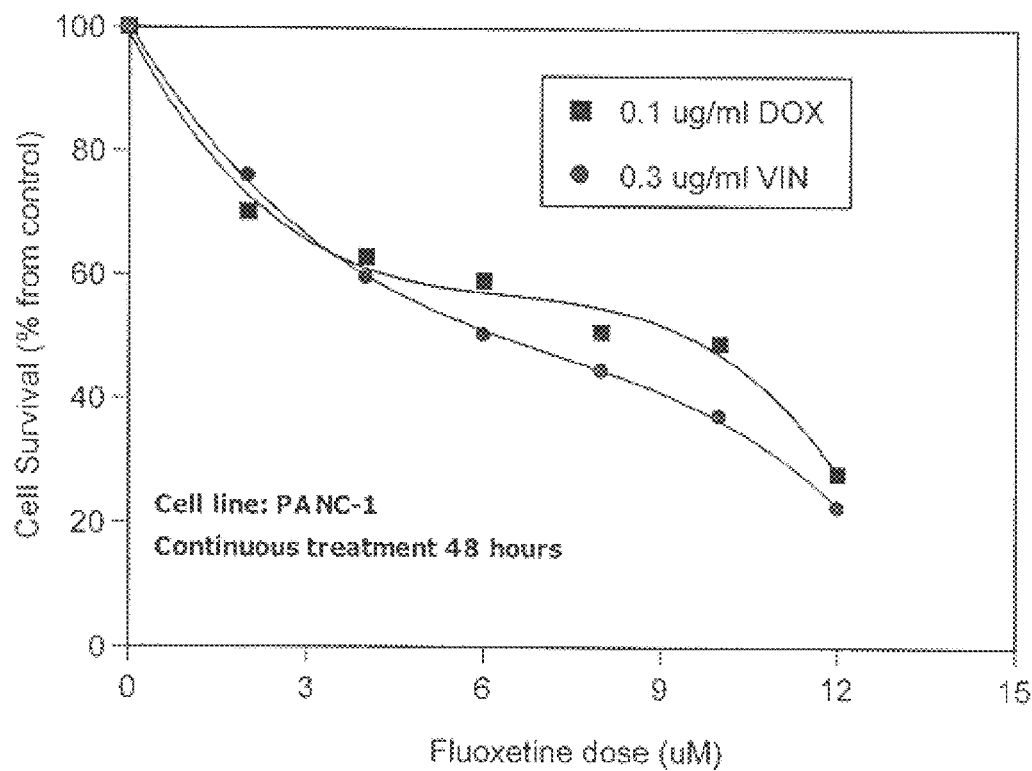
FIG. 3 is a dose response curve for the effects of fluoxetine on the survival of PANC-1 cells treated with 0.1 $\mu$g/ml doxorubicin or, separately, 0.3 $\mu$g/ml vinblastine, 48 hours post administration. The points are experimental, each an average of 32–64 repeats (sd levels which are similar to those in FIGS. 1 and 2, are not shown in order to reduce symbol crowding). The solid curves are non-theoretical, drawn to emphasize the trends in the data.
Figure 4:
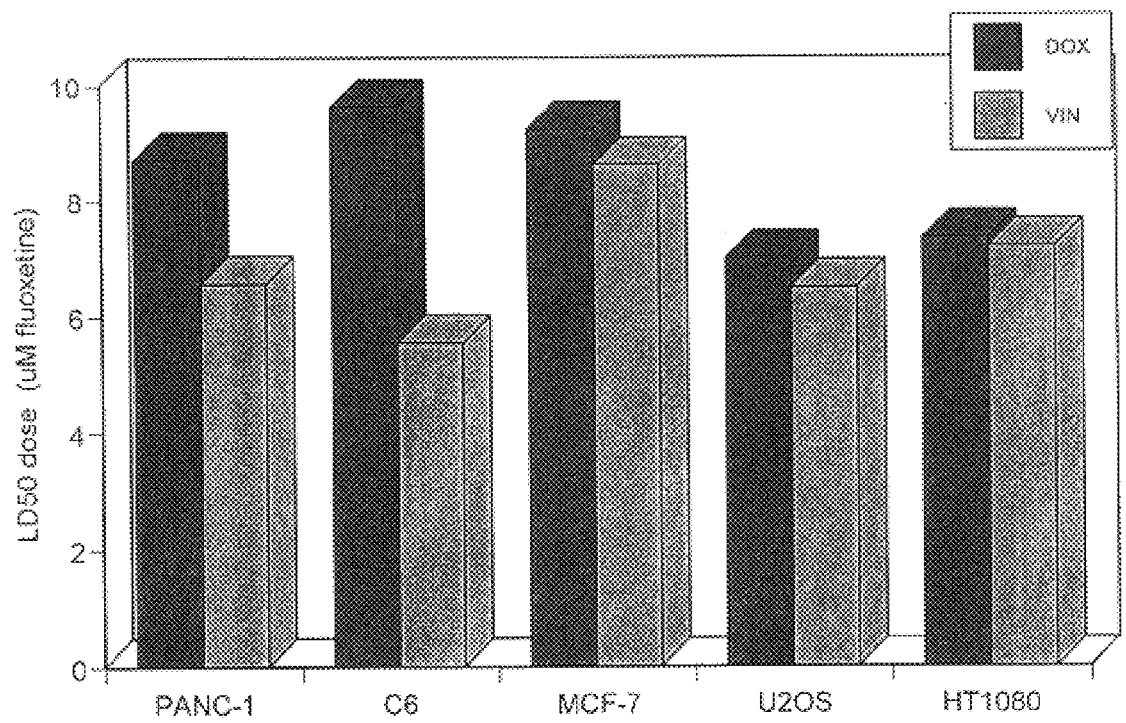
FIG. 4 is a bar-graph demonstrating LD$_{50}$ doses of fluoxetine effect in potentiating tumor treatment by the chemotherapeutic drugs doxorubicin and, separately, vinblastine, for five different cell lines. Data was taken from analysis of dose response curves similar to those shown in FIG. 3, for each of the cell lines, obtained under the same drug species, drug dose and treatment period listed in the legend to FIG. 3.
Figure 5:
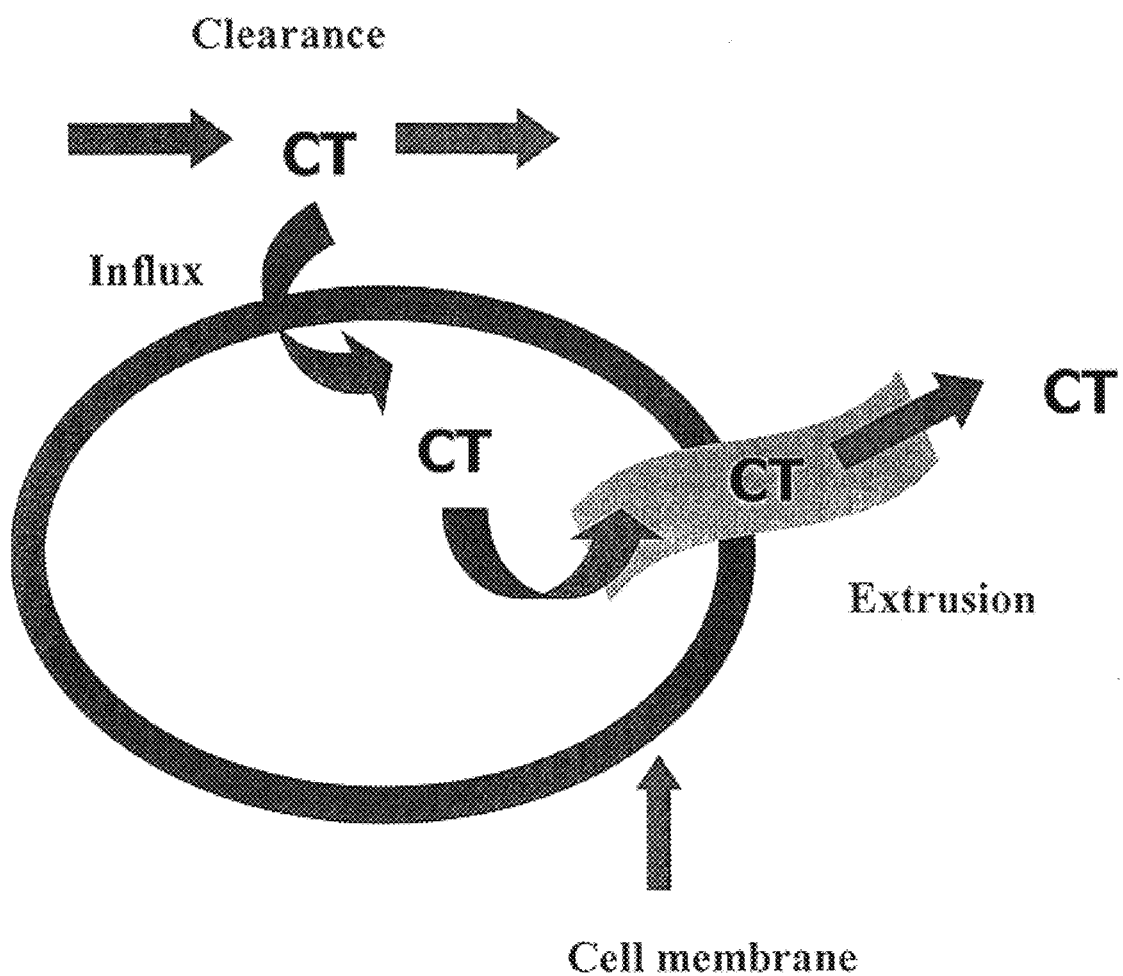
FIG. 5 is a scheme illustrating the MDR mechanism. The chemotherapeutic drug, denoted CT, usually gains entry into the cell by self-diffusion, this influx driven by the electrochemical gradient of the drug across the cell membrane. The intracellular drug concentration is reduced below lethal threshold, by ATP-dependant extrusion through the MDR pumps embedded in the cell membrane.

As expected from the testing with 15 $\mu$M, fluoxetine alone was not toxic to the cells. For the drug species and respective doses tested—0.1 $\mu$g/ml DOX and 0.3 $\mu$g/ml VIN—drugs alone caused 50% and 10–20% reductions in cell survival, for the non-resistant and resistant cell lines, respectively. Normalizing, for each cell line, the survival of cells receiving the chemotherapeutic drug and fluoxetine, to the survival of the cells receiving the chemotherapeutic drug alone (i.e., zero fluoxetine) it was possible to construct fluoxetine dose response curves. A typical example is shown in FIG. 3, for the PANC-1 cell line, with both drugs. From such dose response curves, using computer-aided polynomial curve fitting, it was possible to determine for each drug and each cell line, an $LD_{50}$ for the fluoxetine potentiation effect. These $LD_{50}$ values, for all five cell lines, each with both drugs, are shown in FIG. 4.

Several features of these results are worthy of attention:

First, in all cases fluoxetine potentiates the cytotoxic effect of the chemotherapeutic drug.

Second, the $LD_{50}$ range, which spans from 7–10 $\mu$M fluoxetine and 6.5–8 $\mu$M fluoxetine, for DOX and VIN, respectively, is well below the highest safety limit of 15 $\mu$M fluoxetine. This is completely different than the cases of Verapamil and Cyclosporin, where the dose range for chemosensitization was well above their safety limit and hence impractical for clinical applications.

Third, taking into consideration that in the resistant cell lines the potentiation has to work on double the number of cells than in the non-resistant lines, yet the $LD_{50}$ range is quite similar—these data imply that the potentiation effect is more significant in the MDR lines.

Fourth, in the non-resistant lines, the effect of fluoxetine on a given line is not drug-sensitive while in the resistant lines, fluoxetine is more potent (lower $LD_{50}$) with VIN than with DOX.

Insights into the Operating Mechanisms

Without an intention to limit the present invention in any way, the data presented herein allows speculating some mechanistic insights with respect to the chemosensitization activity of 3-aryloxy-3-phenylpropylamine in general and fluoxetine in particular.

The finding that fluoxetine potentiates the cytotoxicity with different drugs, that have furthermore different killing mechanisms, rules out a drug-specific effect. Could fluoxetine be triggering a cell death mechanism that it totally independent of the presence of the chemotherapeutic drug in the cell? It is suggest this triggering option is unlikely in view of the finding that fluoxetine alone is not toxic to the cells—at the same dose level where it exerts its effect in the presence of a cytotoxic drug. Since the sites of action for the chemotherapeutic drugs are intracellular it is reasonable to assume that fluoxetine exerts its effect(s) inside the cell, also.

In general, nature has not planned for the introduction of foreign matter such as drugs, into living biological systems. Hence nature has made no specific efforts to assist drug entry into cells. That drugs do gain entry into cells is a fact of life. Drugs do it by at least two pathways that are not mutually exclusive: (i) by diffusion across the cell membrane, driven by the drug's electrochemical-potential gradient; and (ii) by "borrowing a ride" on natural transport systems designed (by nature) to transport molecules that a normal component of a living system. Obviously both pathways can operate in both directions, namely influx and efflux. In addition, the interaction of the foreign entity with biological transport systems can take the form of blockage, where a foreign matter blocks the passage of other materials through the transporter.

The data presented herein reveal that fluoxetine acts on both MDR and non-MDR cells, but is more effective with the former type. This raises at least two possibilities for fluoxetine's mechanism(s) of action:

First: Fluoxetine inhibits extrusion channels that pump chemotherapeutic drugs out of the cells, reducing the intracellular drug doses below the lethal threshold. The fact that both MDR and non-MDR cells have been affected, but to different extent, fits with the extrusion pumps being natural proteins that can exist in all cells, but in significantly larger numbers (copies per cell) in MDR cells.

Second: Fluoxetine has two different activities: One is pump inhibition as above especially (and possibly only) in the MDR cells. The other is enhancement of the cellular response to the chemotherapeutic drug, without any change in the intracellular drug level. The latter could operate in the non-MDR cells alone, or in both type of cells.

Figure 6:
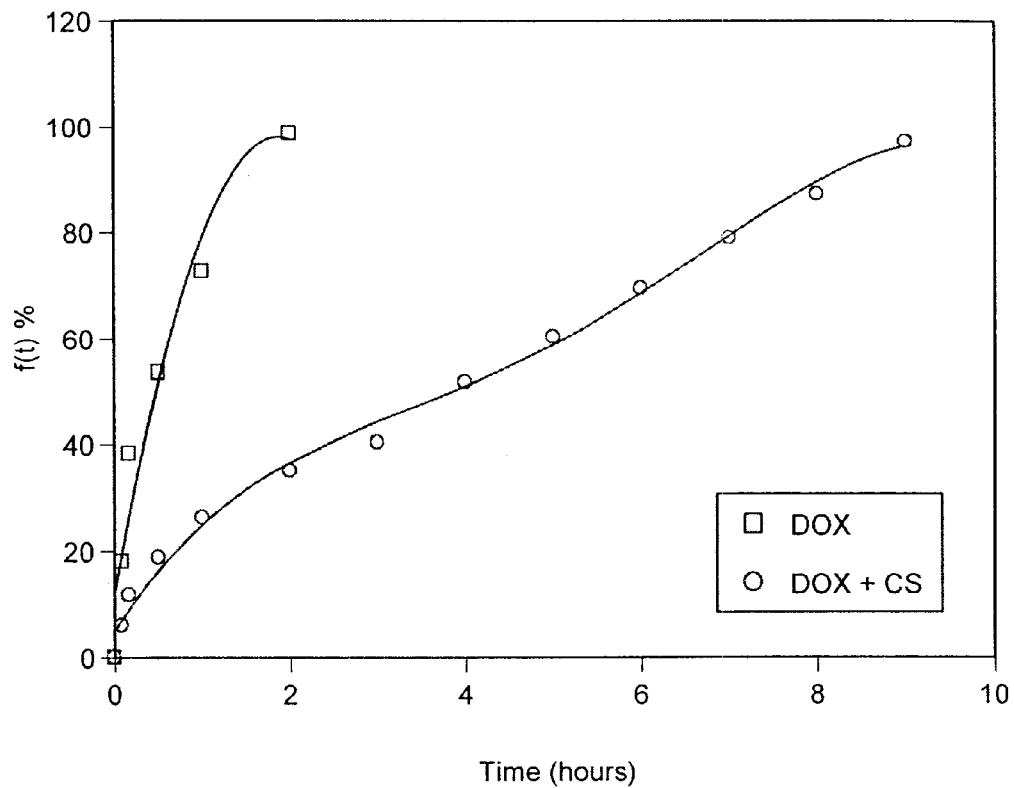
FIG. 6 demonstrates the efflux of intracellular Doxorubicin (DOX) from C6 cells, under unidirectional flux conditions. The efflux is expressed as f(t), the cumulative quantity of DOX that diffused out of the cells at time=t, normalized to the total intracellular DOX concentration at time=0. The points are the experimental data, open squares—for cells loaded with 0.1 $\mu$g/ml DOX and open circles for cells loaded with 0.1 $\mu$g/ml DOX together with 15 $\mu$M fluoxetine. The solid curves are non-theoretical, drawn to emphasize the trends in the data.

An experimental method to support or refute the first mechanism, is the following:

Cells are loaded with non-lethal doses of a chemotherapeutic drug alone, or drug and fluoxetine. Upon completion of loading the extracellular fluid is replaced with buffer alone, and the efflux of drug into the external media is monitored for several hours. If fluoxetine inhibits efflux pumps, drug efflux in the systems receiving the combined treatment should be slower than in those receiving the drug alone. This expectation was met, as shown by the following:

The effect of fluoxetine on DOX efflux from C6 cells was studied as detailed under the Methods section above. The DOX and fluoxetine loading doses were 0.1 $\mu$g/ml and 15 $\mu$M, respectively. The cumulative quantity of DOX that diffused out of the cells at time=t was normalized to the total intracellular concentration of DOX at time=0, and is denoted f(t). The magnitudes of f(t) as function of time are plotted in FIG. 6, for the cells that received DOX alone and for the cells that received DOX with fluoxetine.

The data presented makes it clear that 2 hours suffice for complete depletion of intracellular DOX from cells that were loaded with DOX alone. In contrast, DOX efflux was significantly slower in cells that received both DOX and fluoxetine. At 2 hours, loss of intracellular DOX (in the combined treatment) was under 40%, and complete depletion was 450% slower than in the absence of fluoxetine. The pattern of DOX efflux from the cells loaded with this drug alone fits dominance of a single pathway. Based on previous experience, were the efflux seen for the DOX-alone systems dominated by self diffusion of the drug through the lipid bilayer membranes, at 2 hours f(t) would range from 10–30%. This clearly indicates that the single efflux pathway, that provides 100% depletion at 2 hours, can be assigned to an extrusion pump.

DOX efflux from cells that received the combined treatment is at the least bi-phasic, which indicates that DOX diffuses out of those cells by at least two pathways. The pattern of the fastest pathway, which dominates efflux at the first 30 minutes and accounts for ≦20% of the total depletion, is quite similar to that of the DOX-alone case. The pattern of the remaining 80% fits one or more additional, significantly slower, pathways. These data imply a fluoxetine effect at the transport level, a major part of which is reduction in the number of active pumps, with possible minor effects of reduction in the rate constant of DOX efflux through this pump.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a subject having a cancer with multidrug resistance and being sensitive to the combination below, the method comprising administering to the subject, substantially at the same time, an enhanced chemotherapeutically effective amount of doxorubicin and a chemosensitizing effective amount of at least one 3-aryloxy-3-phenylpropylamine.

2. The method of claim 1, wherein said at least one 3-aryloxy-3-phenylpropylamine is administered orally.

3. The method of claim 1, wherein said at least one 3-aryloxy-3-phenylpropylamine is of the formula:

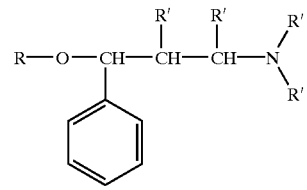

wherein each R' is independently hydrogen or methyl;

R is naphthyl or

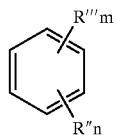

R" and R'" are halo, trifluoromethyl, $C_1$–$C_4$ alkyl, $C_1$–$C_3$ alkoxy or $C_3$–$C_4$ alkenyl; and n and m are 0, 1 or 2; and acid addition salts thereof formed with pharmaceutically acceptable acids.

4. The method of claim 1, wherein said at least one 3-aryloxy-3-phenylpropylamine is selected from the group consisting of 3-(p-isopropoxyphenxoy)-3-phenylpropylamine methanesulfonate, N,N-dimethyl 3-(3',4'-dimethoxyphenoxy)-3-phenylpropylamine p-hydroxybenzoate, N,N-dimethyl 3-(alpha-naphthoxy)-3-phenylpropylamine bromide, N,N-dimethyl 3-(beta-naphthoxy)-3-phenyl-1-methylpropylamine iodide, 3-(2'-methyl-4',5'-dichlorophenoxy)-3-phenylpropylamine nitrate, 3-(p-t-butylphenoxy)-3-phenylpropylamine glutarate, N-methyl 3-(2'-chloro-p-tolyloxy)-3-phenyl-1-methylpropylamine lactate, 3-(2',4'-dichlorophenoxy)-3-phenyl-2-methylpropylamine citrate, N,N-dimethyl 3-(m-anisyloxy)-3-phenyl-1-methylpropylamine maleate, N-methyl 3-(p-tolyloxy)-3-phenylpropylamine sulfate, N,N-dimethyl 3-(2',4'-difluorophenoxy)-3-phenylpropylamine 2,4-dinitrobenzoate, 3-(o-ethylphenoxy)-3-phenylpropylamine dihydrogen phosphate, N-methyl-(2'-chloro-4'-isopropylphenoxy)-3-phenyl-2-methylpropylamine maleate, N,N-dimethyl 3-(2'-alkyl-4'-fluorophenoxy)-3-phenylpropylamine succinate, N,N-dimethyl 3-(o-isopropoxyphenoxy)-3-phenyl-propylamine phenylacetate, N,N-dimethyl 3-(o-)bromophenoxy)-3-phenyl-propylamine beta-phenylpropionate, N-methyl 3-(p-iodophenoxy)-3-phenyl-propylamine propiolate, N-methyl 3-(3-n-propylphenoxy)-3-phenyl-propylamine decanoate, and N-methyl 3-(p-trifluoromethylphenoxy)-3-phenylpropylamine.

5. The method of claim 1, wherein said at least one 3-aryloxy-3-phenylpropylamine is N-methyl 3-(p-trifluoromethylphenoxy)-3-phenylpropylamine or a pharmaceutically-acceptable salt thereof.

6. The method of claim 1, wherein said chemosensitizing effective amount ranges between 1 $\mu$M and 12 $\mu$M.

7. A method of treating a subject having a cancer with multidrug resistance and being sensitive to the combination below, the method comprising administering to the subject an enhanced chemotherapeutically effective amount of doxorubicin and a chemosensitizing effective amount of at least one 3-aryloxy-3-phenylpropylamine, said chemosensitizing effective amount ranges between 2 $\mu$M and 12 $\mu$M.

8. The method of claim 7, wherein said administering of said doxorubicin and said at least one 3-aryloxy-3-phenylpropylamine being performed substantially at the same time.

9. The method of claim 7, wherein said at least one 3-aryloxy-3-phenylpropylamine is administered orally.

10. The method of claim wherein said at least one 3-aryloxy-3-phenylpropylamine is of the formula:

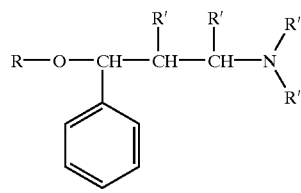

wherein each R' is independently hydrogen or methyl;
R is naphthyl or

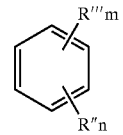

R" and R'" are halo, trifluoromethyl, $C_1$–$C_4$ alkyl, $C_1$–$C_3$ alkoxy or $C_3$–$C_4$ alkenyl; and n and m are 0, 1 or 2; and acid addition salts thereof formed with pharmaceutically acceptable acids.

11. The method of claim 7, wherein said at least one 3-aryloxy-3-phenylpropylamine is selected from the group consisting of 3-(p-isopropoxyphenxoy)-3-phenylpropylamine methanesulfonate, N,N-dimethyl 3-(3',4'-dimethoxyphenoxy)-3-phenylpropylamine p-hydroxybenzoate, N,N-dimethyl 3-(alpha-naphthoxy)-3-phenylpropylamine bromide, N,N-dimethyl 3-(beta-naphthoxy)-3-phenyl-1-methylpropylamine iodide, 3-(2'-methyl-4',5'-dichlorophenoxy)-3-phenylpropylamine nitrate, 3-(p-t-butylphenoxy)-3-phenylpropylamine glutarate, N-methyl 3-(2'-chloro-p-tolyloxy)-3-phenyl-1-methylpropylamine lactate, 3-(2',4'-dichlorophenoxy)-3-phenyl-2-methylpropylamine citrate, N,N-dimethyl 3-(m-anisyloxy)-3-phenyl-1-methylpropylamine maleate, N-methyl 3-(p-tolyloxy)-3-phenylpropylamine sulfate, N,N-dimethyl 3-(2',4'-difluorophenoxy)-3-phenylpropylamine 2,4-dinitrobenzoate, 3-(o-ethylphenoxy)-3-phenylpropylamine dihydrogen phosphate, N-methyl-(2'-chloro-4'-isopropylphenoxy)-3-phenyl-2-methylpropylamine maleate, N,N-dimethyl 3-(2'-alkyl-4'-fluorophenoxy)-3-phenylpropylamine succinate, N,N-dimethyl 3-(o-isopropoxyphenoxy)-3-phenyl-propylamine phenylacetate, N,N-dimethyl 3-(o-)bromophenoxy)-3-phenyl-propylamine beta-phenylpropionate, N-methyl 3-(p-iodophenoxy)-3-phenyl-propylamine propiolate, N-methyl 3-(3-n-propylphenoxy)-3-phenyl-propylamine decanoate, and N-methyl 3-(p-trifluoromethylphenoxy)-3-phenylpropylamine.

12. The method of claim 7, wherein said at least one 3-aryloxy-3-phenylpropylamine is N-methyl 3-(p- trifluoromethylphenoxy)-3-phenylpropylamine or a pharmaceutically-acceptable salt thereof.

13. A pharmaceutical composition comprising as a chemotherapeutically active ingredient an enhanced effective amount of doxorubicin and as a chemosensitization active ingredient at least one 3-aryloxy-3-phenylpropylamine.

14. The pharmaceutical composition of claim 13, wherein said at least one 3-aryloxy-3-phenylpropylamine is of the formula:

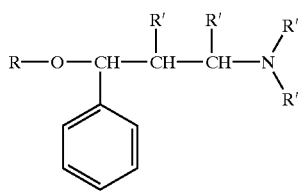

wherein each R' is independently hydrogen or methyl;
R is naphthyl or

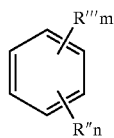

R" and R'" are halo, trifluoromethyl, $C_1$–$C_4$ alkyl, $C_1$–$C_3$ alkoxy or $C_3$–$C_4$ alkenyl; and
n and m are 0, 1 or 2; and acid addition salts thereof formed with pharmaceutically acceptable acids.

15. The pharmaceutical composition of claim 13, wherein said at least one 3-aryloxy-3-phenylpropylamine is selected from the group consisting of
3-(p-isopropoxyphenxoy)-3-phenylpropylamine methanesulfonate,
N,N-dimethyl 3-(3',4'-dimethoxyphenoxy)-3-phenylpropylamine p-hydroxybenzoate,
N,N-dimethyl 3-(alpha-naphthoxy)-3-phenylpropylamine bromide,
N,N-dimethyl 3-(beta-naphthoxy)-3-phenyl-1-methylpropylamine iodide,
3-(2'-methyl-4',5'-dichlorophenoxy)-3-phenylpropylamine nitrate,
3-(p-t-butylphenoxy)-3-phenylpropylamine glutarate,
N-methyl 3-(2'-chloro-p-tolyloxy)-3-phenyl-1-methylpropylamine lactate,
3-(2',4'-dichlorophenoxy)-3-phenyl-2-methylpropylamine citrate,
N,N-dimethyl 3-(m-anisyloxy)-3-phenyl-1-methylpropylamine maleate,
N-methyl 3-(p-tolyloxy)-3-phenylpropylamine sulfate,
N,N-dimethyl 3-(2',4'-difluorophenoxy)-3-phenylpropylamine 2,4-dinitrobenzoate,
3-(o-ethylphenoxy)-3-phenylpropylamine dihydrogen phosphate,
N-methyl-(2'-chloro-4'-isopropylphenoxy)-3-phenyl-2-methylpropylamine maleate,
N,N-dimethyl 3-(2'-alkyl-4'-fluorophenoxy)-3-phenylpropylamine succinate,
N,N-dimethyl 3-(o-isopropoxyphenoxy)-3-phenyl-propylamine phenylacetate,
N,N-dimethyl 3-(o-)bromophenoxy)-3-phenyl-propylamine beta-phenylpropionate,
N-methyl 3-(p-iodophenoxy)-3-phenyl-propylamine propiolate,
N-methyl 3-(3-n-propylphenoxy)-3-phenyl-propylamine decanoate, and
N-methyl 3-(p-trifluoromethylphenoxy)-3-phenylpropylamine.

16. The pharmaceutical composition of claim 13, wherein said at least one 3-aryloxy-3-phenylpropylamine is N-methyl 3-(p-trifluoromethylphenoxy)-3-phenylpropylamine or a pharmaceutically acceptable salt thereof.

* * * * *